(12) United States Patent
Kritikou (10) Patent No.: US 8,470,381 B2
(45) Date of Patent: Jun. 25, 2013

(54) SPINOSYN ANTIFOULING COMPOSITIONS, METHODS OF USE THEREOF AND ARTICLES PROTECTED FROM ATTACHMENT OF BIOFOULING ORGANISMS

(75) Inventor: Christine Kritikou, Kifissia (GR)

(73) Assignees: Christine Kritikou, Kifissia (GR); Entarco S.A., Kifissia (GR)

( * ) Notice: Subject to any disclaimer, the term of this patent is extended or adjusted under 35 U.S.C. 154(b) by 98 days.

(21) Appl. No.: 13/120,123

(22) PCT Filed: Sep. 18, 2009

(86) PCT No.: PCT/IB2009/007041
§ 371 (c)(1),
(2), (4) Date: Mar. 21, 2011

(87) PCT Pub. No.: WO2010/032135
PCT Pub. Date: Mar. 25, 2010

(65) Prior Publication Data
US 2011/0172173 A1    Jul. 14, 2011

Related U.S. Application Data

(60) Provisional application No. 61/099,053, filed on Sep. 22, 2008.

(51) Int. Cl.
*A61K 35/00* (2006.01)
*A61K 31/70* (2006.01)
*C09D 5/16* (2006.01)
*C09D 5/18* (2006.01)

(52) U.S. Cl.
USPC ........ 424/780; 514/28; 106/18.32; 106/18.33

(58) Field of Classification Search
None
See application file for complete search history.

(56) References Cited

U.S. PATENT DOCUMENTS

| | | | |
|---|---|---|---|
| 5,202,242 A | 4/1993 | Mynderse et al. | |
| 5,362,634 A | 11/1994 | Boeck et al. | |
| 5,496,931 A | 3/1996 | Boeck et al. | |
| 5,571,901 A | 11/1996 | Boeck et al. | |
| 5,591,606 A | 1/1997 | Turner et al. | |
| 5,631,155 A | 5/1997 | Turner et al. | |
| 5,670,364 A | 9/1997 | Mynderse et al. | |
| 5,670,486 A | 9/1997 | Mynderse et al. | |
| 5,767,253 A | 6/1998 | Turner et al. | |
| 5,840,861 A | 11/1998 | Mynderse et al. | |
| 6,001,981 A | 12/1999 | DeAmicis et al. | |
| 6,149,927 A | 11/2000 | Ghosh | |
| 6,610,282 B1 | 8/2003 | Ghosh | |
| 6,676,954 B2 | 1/2004 | Dai et al. | |
| 6,706,758 B2 * | 3/2004 | Fischer et al. | 514/473 |
| 6,800,614 B2 | 10/2004 | Lewer et al. | |
| 6,821,526 B1 | 11/2004 | Huang | |
| 6,919,464 B1 | 7/2005 | Crouse et al. | |
| 7,015,001 B2 | 3/2006 | Baltz et al. | |
| 7,205,289 B2 * | 4/2007 | Fischer et al. | 514/183 |
| 7,285,653 B1 | 10/2007 | Eberz et al. | |
| 8,299,036 B2 * | 10/2012 | Funke et al. | 514/30 |
| 2005/0096407 A1 | 5/2005 | Tomko et al. | |
| 2006/0040877 A1 | 2/2006 | Burns et al. | |
| 2008/0095737 A1 | 4/2008 | Matias | |
| 2008/0188427 A1 | 8/2008 | Dick et al. | |

FOREIGN PATENT DOCUMENTS

| | | |
|---|---|---|
| EP | 0375316 A1 | 6/1990 |
| EP | 550788 A1 | 7/1993 |
| EP | 578586 A1 | 1/1994 |
| EP | 0 954 966 A1 | 11/1999 |
| WO | WO 93/09126 A1 | 5/1993 |
| WO | WO 94/20518 A1 | 9/1994 |
| WO | WO 99/60856 A1 | 12/1999 |
| WO | WO 02/077004 A1 | 10/2002 |
| WO | WO 2006/127322 A2 | 11/2006 |
| WO | WO 2009/054003 A1 | 4/2009 |

OTHER PUBLICATIONS

Kirst et al. (2010) The Journal of Antibiotics 63, 101-111.*
Rouhi, A. Maureen, The Squeeze on Tributyltins, Chemical Engineering News, Apr. 27, 1998, pp. 41-42.
Kirst et al., Unique Fermentation-Derived Tetracyclic Macrolides, Tetrahedon Letters, A83543A-D, 32:4839-4842, (1991).
Avelin et al., J. Chem. Ecol., 19(10), 2155-67 (1993).
GEFSEC Project ID 2932, "Alternatives to DDT Usage in the Production of Antifouling Paint".
Rittschof D., Clare AS, Gerhart DJ, Avelin Mary, Bonaventura J "Barnacle in vitro Assays for Biologically Active Substances: Toxicity and Settlement Assays Using Mass Cultured *Balanus Amphitrite Amphitrite* Darwin, *Biofouling*" 6:115-122, (1991).
Targett, "Allelochemistry in Marine Organisms: Chemical Fouling and Antifouling Strategies" (1998).

* cited by examiner

*Primary Examiner* — Chris R Tate
*Assistant Examiner* — Russell Fiebig
(74) *Attorney, Agent, or Firm* — Finnegan, Henderson, Farabow, Garrett & Dunner, LLP (57) ABSTRACT

Disclosed herein are antifouling compositions including at least one spinosyn active material. These compositions provide protection to surfaces coated or impregnated therewith from attachment of various biofouling organisms. Compositions include, for example, paint, varnish, and sealant formulations.

6 Claims, 3 Drawing Sheets

Figure 1. The growth of *Dunaliella tertiolecta* monitored through the log and lag phase in the presence of various concentrations of spinosad.

SPINOSYN ANTIFOULING COMPOSITIONS, METHODS OF USE THEREOF AND ARTICLES PROTECTED FROM ATTACHMENT OF BIOFOULING ORGANISMS

This application claims priority to U.S. Patent Application No. 61/099,053, filed on Sep. 22, 2008, the contents of which are incorporated herein by reference.

The present invention relates to spinosyn compositions which impart marine or freshwater antifouling properties. Specifically, compositions of the present invention lend protection to surfaces by preventing attachment of various biofouling organisms. The present invention also relates to coating compositions that lend surface protection to surfaces coated therewith from attachment of various biofouling organisms. These compositions are advantageously used in paint, varnish, primer and sealant formulations.

Biocides are commonly used in a variety of coating materials having diverse applications. In marine paints, for example, biocides protect underwater structures against attachment of a wide range of biofouling organisms, such as algae, barnacles, ship worms and other aquatic nuisance species. In lakes and rivers, biocides are used to protect underwater structures from freshwater organisms, such as zebra mussels. It has been found that microorganisms, their viscous, bio-organic product and absorbed organic matter constitute a tenacious slime which forms on the surfaces of submerged structures. The initial organisms in this fouling sequence are bacteria, followed by a biotic progression of diatoms, hydrids, algae, bryozoans, protozoans and finally macrofoulants. Macrofoulants tend to be rugophilic, i.e., settling on roughened surfaces in preference to smooth surfaces.

The hull of a ship is constantly immersed in water for several years and the buildup of these same marine organisms can lead to a significant hydrodynamic drag on the ship. This drag on a ship impedes its passage through the water resulting in increased fuel usage, causing higher operational and environmental costs. It has been estimated that it would cost the shipping industry $3 billion annually in added fuel costs if the hulls of ships were left untreated. Additional costs occur when the ship is placed in dry dock. These include the cost to clean the hull and the down time, which are estimated at $2.7 billion annually. In addition, environmental costs not only result from increased consumption of fossil fuels (a nonrenewable resource) but also increased amounts of carbon dioxide (a greenhouse gas) and other atmospheric pollutants (nitrogen oxides, sulfur oxides, unburned hydrocarbons, ozone etc.). Rouhi, A. Maureen; The Squeeze on Tributyltins. Chem. Eng. News. Apr. 27, 1998, 41-42. The problem of fouling is not limited to ships, however, but extends to other underwater structures, as well. Buoys can shift due to the excessive weight of fouling organisms. The fouling of intake screens of municipal water supply systems can lead to reduced flow rates and accelerated corrosion. Concrete or ferro-cement structures, e.g., dams, are also adversely affected by biofouling organisms.

An ideal antifouling biocide should be effective, show broad-spectrum activity, and should be stable in the formulated end product. In addition the ideal biocide should have the following environmental characteristics: i) rapid degradation in the environment, ii) rapid partitioning in the environment, resulting in limited bioavailability to non-target organisms, iii) minimal toxicity to non-target organisms at the concentrations present in the environment, iv) minimal bioaccumulation of toxicologically significant compounds.

Environment protection is an important issue, considering that the volume of antifouling paints used worldwide is very high. According to GEFSEC PROJECT ID 2932 (Alternatives to DDT usage in the production of antifouling paint), China, for example, consumes annually about 65,000 MT of antifouling paint. Due to environmental concerns, the application of triorganotin-based paints has been prohibited. Tributyltin (TBT) based paints pose a substantial risk of toxicity and can have a chronic impact on species, habitats and ecosystems. Cuprous oxide and zinc oxide, which are other commercially used antifoulants, function by releasing heavy metals, i.e., copper and zinc, unfortunately copper is touted as a harmful toxin, especially in the marine environment. Therefore, safer biocides should be selected as soon as possible before new serious environmental problems are found. Manufacturers of such products are faced with the prospect of changing existing formulations to include alternative agents that are, at once, effective in preventing attachment and growth of biofouling organisms and environmentally benign. Other criteria that must be taken into account in developing acceptable substitutes for ecologically harmful biocides include chemical compatibility with other components in the coating composition, physical compatibility with the dried film and substrate to which the coating is applied, the safety of those handling or using the substitute agents themselves or coating materials containing them and the cost of their production.

Depending upon the particular marine or freshwater structure to be protected, the compositions of the present invention can be directly incorporated into the structure, applied directly to the structure, or incorporated into a coating which is then applied to the marine structure.

In accordance with one aspect, the present invention provides a composition comprising (i) at least one spinosyn or derivative or salt thereof and (ii) a film forming agent or a material into which spinosyn has been incorporated.

The spinosyn or derivative or salt thereof is present in the composition in an amount effective to inhibit the attachment of biofouling organisms on a surface to which the composition is applied as a coating or incorporated.

Also in accordance with this invention, there is provided an antifouling paint composition comprising at least one spinosyn or derivative or salt thereof and a film forming agent.

There is also provided in accordance with the invention, methods of using the antifouling compositions and coating materials including at least one spinosyn. One such method involves protecting a surface exposed to an aqueous environment from fouling organisms present in the aqueous environment by applying to such surface a composition or coating including at least one spinosyn. As another aspect of this invention, articles are provided which have a coating of the composition described herein on at least a portion of the surface thereof, which provides protection against exposure to the deleterious effects of biofouling organisms.

The coating composition described above satisfies one or more of the above-noted criteria for an environmentally acceptable coating product, and in one embodiment satisfies all of the above-noted criteria, in that it provides effective protection against attachment and growth of biofouling organisms, while producing no known ecologically harmful effect. Although spinosyns and spinosad in particular may be toxic to a wide range of aquatic organisms, the environmental risk of spinosyns is minimal, because only organisms in contact with ship's hull are exposed to toxic levels. Spinosad is stable as part of the coating on a ship, but even if it is released (leached) slowly from the hull of the ship, it rapidly degrades to compounds that are essentially nontoxic. Dow Agrosciences LLC, main producer of spinosyns, was presented by the U.S. Environmental Protection Agency, with the Presidential Green Chemistry Challenge Award in the past for spinosad and in 2008 for spinetoram as well, since both products adhere to the principles of green chemistry and it is important to find solutions that also contribute to the preservation of our planet. As described in U.S. Patent Application No. 2008/0188427 incorporated herein by reference, Spinosyns, and Spinosad in particular, have been found to be effective in controlling ectoparasitic infestations in aquaculture raised fish, resulting in improved fish production, thus proving the advantageous profile of spinosyns even when used in an aquatic environment.

Spinosyns, and most specifically spinosad, have been found to be particularly effective antifouling agents, as will be described in detail hereinbelow.

Spinosyns are known fermentation products derived from the naturally occurring bacteria *Saccharopolyspora spinosa*. The family of compounds derived from this bacteria are generally known as spinosyns and have been referred to as factors or components A, B, C, D, E, F, G, H, I, J, K, L, M, N, O, P, Q, R, S, T, U, V, W, Y, and the like, as described in U.S. Pat. Nos. 5,362,634, and 6,821,526 and published applications WO 93/09126 and WO 94/20518, which are each incorporated herein by reference in their entirety. The spinosyn compounds consist of a 5,6,5-tricyclic ring system, fused to a 12-membered macrocyclic lactone, a neutral sugar (rhamnose), and an amino sugar (forosamine) (see Kirst et al. "Unique Fermentation-derived Tetracyclic macrolides, *Tetrahedon Letters*, A83543A-D, 32:4839-4842, (1991)). As used herein, the term "spinosyn" refers to a class of compounds which are based upon the fermentation products from the naturally occurring bacteria, *Saccharopolyspora spinosa* (species and subspecies) or a biologically modified form of this bacteria or combinations thereof. Natural spinosyn compounds may be produced via fermentation from cultures deposited as NRRL 18719, 18537, 18538, 18539, 18743, 18395, and 18823 of the stock culture collection of the Midwest Area Northern Regional Research Center, Agricultural Research Service, United States Department of Agriculture, 1815 North University Street, Peoria, Ill. 61604. Spinosyn compounds are also disclosed in U.S. Pat. Nos. 5,496,931, 5,670,364, 5,591,606, 5,571,901, 5,202,242, 5,767,253, 5,840,861, 5,670,486 and 5,631,155. As used herein, the term "spinosyn" is intended to include natural factors and semi-synthetic derivatives of the naturally produced factors. A large number of chemical modifications to these spinosyn compounds have been made, sometimes referred to as spinosoids and are disclosed in U.S. Pat. No. 6,001,981, hereby incorporated by reference. The term "spinosyn" also includes the novel biologically-active compounds as described in U.S. Patent No. 2006/0040877 produced by methods of using the hybrid polyketide synthase DNA to change the products made by spinosyn producing strains. Finally, the term "spinosyn" includes new spinosyn derivatives produced using the cloned *Saccharopolyspora spinosa* DNA as described in U.S. Pat. No. 7,015,001. Different patterns of control may be provided by biosynthetic intermediates of the spinosyns or by their derivatives produced in vivo, or by derivatives resulting from their chemical modification in vitro. Such biosynthetic intermediates of the spinosyns are considered to belong to the class of "spinosyns" as described herein for use in the present invention.

Spinosyns and derivatives thereof can also exist in the form of salts. The salts are prepared by contacting the free base form with a sufficient amount of the desired acid to produce a salt. By way of non-limiting example, spinosyns can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic, acids. Additionally, by way of non-limiting example, an acid function can form salts including those derived from alkali or alkaline earth metals and those derived from ammonia and amines. Examples of cations include sodium, potassium, magnesium, and aminium cations.

The term spinosyn also includes all isomers of the compounds, including individual stereoisomers i.e. geometric, diastereomers, and enantiomers as well as racemic mixtures, optically active mixtures, and combinations thereof.

In addition the term "spinosyn" as used herein, refers to spinosyns produced by any fungal strains capable of producing spinosyn, i.e. fungal strains belonging to the genus *Aspergillus*, as mentioned in Patent application WO/2009/054003 hereby incorporated by reference.

Spinosad is an insecticide produced by Dow AgroSciences (Indianapolis, Ind.) that is comprised mainly of approximately 85% spinosyn A and approximately 15% spinosyn D. Spinosad is an active ingredient in several insecticide formulations available commercially from Dow AgroSciences LLC, including, for example, those marketed under the trade names TRACER®, SUCCESS®, SPINTOR®, LASER®, and ENTRUST®. The TRACER® product, for example, is comprised of about 44% to about 48% Spinosad (w/v), while ENTRUST® is a white to off-white solid powder containing about 80% Spinosad.

Spinosad, is also commercially available by the company Sigma-Aldrich for R&D purposes, as an analytical standard, at a purity of approximately 98% and is comprised mainly of approximately 70% spinosyn A and 30% spinosyn D.

Spinetoram is a semi-synthetic spinosyn, available commercially from Dow AgroSciences LLC in several insecticide formulations, including, for example, those marketed under the trade names DELEGATE® and RADIANT®. Spinetoram is the common name for a mixture of 50-90% (2R,3αR,5αR,5βS,9S,13S,14R,16αS,16βR)-2-(6-deoxy-3-O-ethyl-2,4-di-O-methyl-α-L-mannopyranosyloxy)-13-[(2R,5S,6R)-5-(dimethylamino)tetrahydro-6-methylpyran-2-yloxy]-9-ethyl-2,3,3α,4,5,5α5β,6,9,10,11,12,13,14,16α,6β-hexadecahydro-14-methyl-1H-as-indaceno[3,2-d]oxacyclododecine-7,15-dione, and 50-10% (2R,3αR,5αS,5βS,9S,13S,14R,16αS,16βS)-2-(6-deoxy-3-O-ethyl-2,4-di-O-methyl-α-L-mannopyranosyloxy)-13-[(2R,5S,6R)-5-(dimethylamino)tetrahydro-6-methylpyran-2-yloxy]-9-ethyl-2,3,3α,5α,5β,6,9,10,11,12,13,14,16α,16β-tetradecahydro-4,14-dimethyl-1H-as-indaceno[3,2-d]oxacyclododecine-7,15-dione. Synthesis of the components of spinetoram is described in U.S. Pat. No. 6,001,981. Macrolide insecticides related to the spinosyns have been also isolated from *Saccharopolyspora pogona*. LW107129 (NRRL 30141 and mutants thereof). These compounds are disclosed in U.S. Pat. No. 6,800,614, hereby incorporated by reference. These compounds are characterized by the presence of reactive functional groups that make further modifications possible at locations where such modifications were not feasible in previously disclosed spinosyns. Natural and semi-synthetic derivatives of the butenyl spinosyns are disclosed in U.S. Pat. No. 6,919,464, hereby incorporated by reference. The term "butenyl-spinosyn"—also called pogonin—as used herein is intended to include natural factors and semi-synthetic derivatives of the naturally produced factors or combinations thereof and it is considered to belong to the same class of "spinosyns" as described herein for use in the present invention.

Spinosad has been shown to be highly effective in the control of certain mites and insects including, but not limited to species from the orders of Lepidoptera, Diptera, Hymenoptera, Thysanoptera, and a few Coleoptera. In addition, formulations comprising Spinosad have been shown to be highly effective when used in agriculture, horticulture, greenhouses, golf courses, gardens, homes, and the like.

Spinosad acts as a stomach and contact poison. Generally, the immediate effect of ingestion is the cessation of feeding, followed 24 hours later by paralysis and death. This compound is a neurotoxin with a novel mode of action involving the nicotinic acetylcholine receptor and GABA receptors.

While spinosyns have heretofore been known to be effective when ingested by insects and mites thereby causing rapid excitation of the nervous system, their use as an antifouling agent had not been investigated and/or proposed so far. Moreover, as it is stated in U.S. Pat. No. 7,285,653 "spinosyns exhibit a strongly insecticidal but no antibacterial activity".

The present inventor has found out that spinosyn and most specifically spinosad, exhibits significant antibacterial properties against some bacteria associated with common fouler *Balanus amphitrite* and belonging to the species *vibrio* sp., *flavobacterium* sp., *alcaligenes* sp. and *aeromonas* sp. These bacteria are derived from bacterial microflora associated with barnacles. These isolates are characterized by morphological and biochemical tests down to the level of genera only.

In addition, the present inventor has found out that spinosyn and spinosad in particular, exhibits excellent antifouling activity on the settlement of barnacle cyprids on surfaces with an effective concentration $EC_{50}$ of $7 \times 10^{-8}$ mg/ml in the absence of any mortality against cyprids. Moreover, the present inventor has created some coating compositions that have been found to be very effective when used as an antifouling marine or freshwater coating.

As used herein, the terms "effective," "effective in the control of," and "effective for control" or "control" are all used interchangeably and all refer to the ability of the active-containing composition to reduce the degree of adherence of at least one species of organisms, over a certain period of time, compared to a composition that does not contain the active compound.

As used herein, the term "antifouling agent", is an agent used to control the growth and settlement of fouling organisms (microbes and higher forms of plant or animal species) on vessels, aquaculture equipment or other structures used in water.

As used herein, the term "biofouling organisms" refers to any and all organisms that participate in the fouling sequence in both saltwater and freshwater environments, including, without limitation, bacteria, diatoms, hydroids, algae, bryozoans, protozoans, ascidians, tube worms, asiatic clams, zebra mussels and barnacles. Generally, barnacles, tubeworms, algae, seaweed and brown and red bryozoans are the organisms that cause the greatest concern in salt and brackish waters. Zebra mussels are the organisms that cause the most fouling problems in freshwater of temperate and subtropical areas.

Barnacles belong to the phylum Arthropoda, subphylum Crustacea, order Sessilia, family Balanidae, genus *Balanus*. They are exclusively marine and, unlike other crustaceans, are all sessile. There are more than 600 species worldwide, and many are colorful animals, for example, red, orange, purple, pink and striped. The majority are a few centimeters in diameter, with some considerably larger. Most are found in the intertidal zone. Those living in shallow-water communities are either typical fouling balanids or commensals.

Twenty-two species of barnacles are reported in the Indian Ocean. Non limited examples are *Balanus amphitrite, Balanus uariegatus, Megabalanus antillensis, Chthamalus malayensis, Chthamalus withersi*, and *Lapas anatifera*. All these species have broad geographic ranges. All *Chthamalus* species, *Lepas* species, and *Balanus amphitrite* prefer waters of near normal salinities.

Marine algae vary in size from one-celled organisms a few millimeters in diameter, to highly organized plants attaining a length of 30 meters. All algae capable of photosynthetic activity contain the pigment chlorophyll, which is enclosed in cell inclusions called chloroplasts. A single algal cell may contain one or more chloroplasts. Micro algae (diatoms) are major components of films formed on the surface of a marine structure as it becomes fouled and may play a role in the ecology of these films.

Diatoms belong to the class Bacillariophyceae. A major characteristic of many benthic diatoms is their ability to become permanently attached to surfaces. This is important both ecologically and economically as diatoms constitute at least a portion of the organisms that foul marine structures. For example, diatoms of the following genus (*Dunaliella, Nitzschia, Skeletonema, Chaetoceros*) and species (i.e. *Dunaliella tertiolecta, Skeletonema costatum*) are important to control.

According to one embodiment, the at least one spinosyn may be added to a material of construction for the production of marine articles. The at least one spinosyn may be mixed with a carrier and/or incorporated directly into the construction materials, for example, cement, plastic, polymer, rubber, elastomeric material, or fiberglass, for the protection of objects subject to biofouling. Structures such as wood pilings and fish nets may be protected by directly incorporating the compositions of the invention into the structure. For example, a composition of the invention, further comprising a carrier, may be applied to wood used for pilings by means of pressure treatment or vacuum impregnation. These compositions may also be incorporated into a fishnet fiber during manufacture.

According yet to another embodiment, the marine coatings containing the compositions of the invention may be applied to a structure to be protected by any of a number of conventional means, such as, for example, spraying, rolling, brushing, impregnating and dipping. Fishnets, for example, may be protected by dipping the fishnets into a composition comprising the compositions of the invention and a carrier or by spraying the fishnets with the composition. Spinosyns can be used with both aqueous and organic solvents as well understood in the art.

According to another embodiment, spinosyns may be included in a conventional paint composition as the sole antifouling agent, or added in combination with other microbicides, antifouling agents, fungicides, herbicides, insecticides, antibiotics, non toxic antifoulants, and natural products or extracts to produce an additive or synergistic effect on attachment of biofouling organisms. Suitable microbicides which may be added in combination with the spinosyn of the present invention include, but are not limited to: 5-chloro-2-methyl-3-isothiazolone; 2-methyl-3-isothiazolone; 2-n-octyl-3-isothiazolone; 4,5-dichloro-2-n-octyl-3-isothiazolone; 3-iodo-2-propynyl butyl carbamate; 1,2-dibromo-2,4-dicyanobutane; methylene-bis-thiocyanate; 2-thiocyanomethylthiobenzothiazole; tetrachloroisophthalonitrile; 5-bromo-5-nitro-1,3-dioxane; 2-bromo-2-nitopropanediol; 2,2-dibromo-3-nitrilopropionamide; N,N'-dimethylhydroxyl-5,5'-dimethylhydantoin; bromochlorodimethylhydantoin; 1,2- benzisothiazolin-3-one; 4,5-trimethylene-2-methyl-3-isothiazolone; 5-chloro-2-(2,4-dichlorophenoxy)phenol and 3,4,4'-trichlorocarbanilide. Suitable marine antifouling agents which may be added in combination with the spinosyn of the present invention include, but are not limited to: manganese ethylenebisdithiocarbamate; zinc dimethyl dithiocarbamate; 2-methyl-4-t-butylamino-6-cyclopropylamino-s-triazine; 2,4,5,6-tetrachloroisophthalonitrile; N,N-dimethyl dichlorophenyl urea; zinc ethylenebisdithiocarbamate; copper thiocyanate; 4,5-dichloro-2-n-octyl-3-isothiazolone; N-(fluorodichloromethylthio)-phthalimide; N,N-dimethyl-N'-phenyl-N'-fluorodichloromethylthio-sulfamide; zinc 2-pyridinethiol-1-oxide; tetramethylthiuram disulfide; 2,4,6-trichlorophenylmaleimide; 2,3,5,6-tetrachloro-4-(methylsulfonyl)-pyridine; 3-iodo-2-propynyl butyl carbamate; diiodomethyl p-tolyl sulfone; bis dimethyl dithiocarbamoyl zinc ethylenebisdithiocarbamate; phenyl(bispyridil)bismuth dichloride; 2-(4-thiazolyl)-benzimidazole; pyridine triphenyl borane; phenylamides; halopropargyl compounds; or 2-haloalkoxyaryl-3-isothiazolones. Suitable 2-haloalkoxyaryl-3-isothiazolones include, but are not limited to, 2-(4-trifluoromethoxyphenyl)-3-isothiazolone, 2-(4-trifluoromethoxyphenyl)-5-chloro-3-isothiazolone, and 2-(4-trifluoromethoxyphenyl)-4,5-dichloro-3-isothiazolone, organometallic anti-foulants, such as tributyl tin or triphenyl tin, or inorganic antifoulants such as for example zinc oxide, copper, copper oxide or dicopper oxide and sulphur dioxide. Suitable agricultural fungicides which may be added in combination with the spinosyn of the present invention include, but are not limited to: dithiocarbamate and derivatives such as ferbam, ziram, maneb, mancozeb, zineb, propineb, metham, thiram, the complex of zineb and polyethylene thiuram disulfide, dazomet, and mixtures of these with copper salts; nitrophenol derivatives such as dinocap, binapacryl, and 2-sec-butyl-4,6-dinitrophenyl isopropyl carbonate; heterocyclic structures such as captan folpet, glyodine, dithianon, thioquinox, benomyl, thiabendazole, vinolozolin, iprodione, procymidone, triadimenol, triadimefon, bitertanol, fluoroimide, triarimol, cycloheximide, ethirimol, dodemorph, dimethomorph, thifluzamide, and, quinomethionate; miscellaneous halogenated fungicides such as: chloranil, dichlone, chloroneb, tricamba, dichloran, and polychloronitrobenzenes; fungicidal antibiotics such as: griseofulvin, kasugamycin and streptomycin; miscellaneous fungicides such as: diphenyl sulfone, dodine, methoxyl, 1-thiocyano-2,4-dinitrobenzene, 1-phenylthiosemicarbazide, thiophanate-methyl, and cymoxanil; as well as acylalanines such as, furalaxyl, cyprofuram, ofurace, benalaxyl, and oxadixyl; fluazinam, flumetover, phenylbenzamide derivatives such as those disclosed in EP 578586 A1, amino acid derivatives such as valine derivatives disclosed in EP 550788 A1, methoxyacrylates such as methyl (E)-2-(2-(6-(2-cyanophenoxy)pyrimidin-4-yloxy)phenyl)-3-methoxyacrylate; benzo(1,2,3)thiadiazole-7-carbothioic acid S-methyl ester: propamocarb; carbendazim; myclobutanil; fenbuconazole; tridemorph; pyrazophos; fenarimol; fenpiclonil; and pyrimethanil. Suitable herbicides which may be added in combination with the spinosyn of the present invention include, but are not limited to: carboxylic acid derivatives, including benzoic acids and their salts; phenoxy and phenyl substituted carboxylic acids and their salts; and trichloroacetic acid and its salts; carbamic acid derivatives, including ethyl N,N-di(n-propyl)thiolcarbamate and pronamide; substituted ureas, substituted triazines, diphenyl ether derivatives such as oxyfluorfen and fluoroglycofen, anilides such as propanil, oxyphenoxy herbicides, uracils, nitriles, and other organic herbicides such as dithiopy and, thiazopyr. Suitable insecticides which may be added in combination with the spinosyn of the present invention include, but are not limited to: abamectin, bifenthrin; cyfluthrin; cyhexatin; cypermethrin; cyphenothrin; clothianidin, deltamethrin; endosulfan; -oxide; fenoxycarb; fensulfothion; fenvalerate; flucycloxuron; flufenoxuron; fluvalinate; furathiocarb; imidacloprid, isazophos; isofenphos; isoxathion; methiocarb; methomyl; mexacarbate; nicotine; permethrin and resmethrin. Non-limited examples of non-toxic and natural antifouling agents include decalactone, alantolactone, zosteric acid and capsaicin. A typical example of a suitable antibiotic is tetracycline, which is a registered antifoulant. According to yet another embodiment, antifouling compositions as disclosed in U.S. Patent Application No. 2008/0095737, may also be combined with the at least one spinosyn antifouling agent of the present invention.

The carrier component combined with at least one spinosyn can be a film-forming component, a thermoplastic material, fiberglass, an elastomeric component, vulcanized rubber, or a cementitious component. The carrier component can be any component or combination of components which incorporates the antifouling agent or it is applied easily to the surface to be protected and adheres to the surface to be protected when the surface is submerged. The cementitious compounds are used to protect certain types of underwater structures, as are the elastomeric materials and vulcanized rubber. Different components will have different desired properties depending on the material comprising the underwater surface, the operation requirements of the surface, the configuration of the surface, and the antifouling compound. After a surface is provided with a protective coating in accordance with this invention, spinosyn that is present in the coating comes in contact with biofouling organisms, thereby preventing their attachment. Marine coatings comprise a film forming agent and solvent and optionally other ingredients. The solvent may be either organic solvent or water. The compositions of the invention are suitable for use in both solvent and water based marine coatings. Any conventional film forming agent may be utilized in the marine antifouling coating incorporating the compositions of the invention. Film-forming components may include polymer resin solutions. Non-limiting examples of polymer resins include unsaturated polyester resins formed from (a) unsaturated acids and anhydrides, such as maleic anhydride, fumaric acid, and itaconic acid; (b) saturated acids and anhydrides, such as phthalic anhydride, isophthalic anhydride, terephthalic anhydride, tetrahydrophthalic anhydride, tetrahalophthalic anhydrides, chlorendic acid, adipic acid, and sebacic acid; (c) glycols, such as ethylene glycol, 1,2 propylene glycol, dibromoneopentyl glycol, Dianol 33®, and Dianol 22®; and (d) vinyl monomers, such as styrene, vinyl toluene, chlorostyrene, bromostyrene, methylmethacrylate, and ethylene glycol dimethacrylate. Other suitable resins include but are not limited to vinyl ester-, vinyl acetate-, and vinyl chloride-based resins, vinyl chloride-vinyl acetate copolymer systems as aqueous dispersions or solvent based systems, mixtures of natural rosin and vinyl chloride-vinyl acetate copolymers, acrylic resins in solvent based or aqueous systems, urethane-based resins, self-polishing copolymer resins, ablative resins, leaching resins, elastomeric components, vulcanized rubbers, butadiene-styrene rubbers, butadiene-acrylonitrile rubbers, butadiene-styrene-acrylonitrile rubbers, drying oils such as linseed oil, asphalt, epoxies, siloxanes like for example polydimethylsiloxane, silanes like alkyl and aryl alkoxy silanes, silicones and silicone-based technologies like fluorosilicones, silicone acrylates, silicone latex elastomers, and combinations thereof.

The coating composition of the invention may include components in addition to spinosyns and a film-forming component, so as to confer one or more desirable properties, such as increased or decreased hardness, strength, increased or decreased rigidity, reduced drag, increased or decreased permeability, or improved water resistance. The selection of a particular component or group of components to impart such properties are within the capabilities of those having ordinary skill in the art. The marine coatings of the present invention may optionally contain one or more of the following: inorganic pigments, organic pigments or dyes, natural resins, such as rosin, fillers, extenders, swelling agents, wetting agents, coalescents, plasticizers, dispersants, surface active agents, preservatives, rheology modifiers or adhesion promoters, UV filters, and combinations thereof.

The primary active ingredient for use in the present invention comprises at least one spinosyn from the class of spinosyns as described above. The percentage of spinosyn in the coating composition required for effective protection against biofouling organisms may vary substantially depending on the nature of the marine or freshwater structure to which the coating composition is applied, the service in which the structure is used, the pH of water and other environmental conditions to which the structure is exposed, depending on the spinosyn itself, the chemical nature of the film former, as well as other additives present in the composition that may influence the effectiveness of spinosyn. The upper limit of activity may be also driven by characteristics of cost and toxicity that would be readily apparent to the skilled artisan. One skilled in the art would recognize that the amount of spinosyn could be reduced in the event a second active ingredient were present, so long as the combined composition is active as an antifoulant.

According to one embodiment, the spinosyn is present in the composition in an amount in the range from 0.001% to 90% w/w. According to another embodiment, the spinosyn is present in an amount in the range from 0.1% to 25% w/w. According to yet another embodiment, the spinosyn is present in an amount in the range from 1% to 10% w/w.

Spinosyns may be included in a paint formulation during the paint manufacturing processes or added to the paint at the time of use. Spinosyns can be simply mixed into the film-forming components or may be covalently bound to the resin, known as "ablative or self-polishing coating" which is released only after the bond hydrolyzes in seawater. Controlled hydrolysis permits a slow release rate while creating a hydrophilic site on the resin. A new layer of spinosyn is then exposed when the hydrolyzed layer is washed away. A non-limiting example of self-polishing antifouling compositions are mentioned in US patent application 2005/0096407 incorporated herein by reference. The antifouling agent spinosyn, can be included in the marine coating composition neat as a particulate solid, in an encapsulated particulate form, for example, in which individual chelate particles are embedded in a matrix of bentonite or silica, in nanoparticles, or as a suspension in a liquid medium. Furthermore, spinosyns may be used in various controlled release compositions, like for example those mentioned in U.S. Pat. No. 6,610,282, U.S. Pat. No. 6,149,927, and U.S. Pat. No. 6,676,954. In a controlled release composition spinosyn may be incorporated with slow release materials which permit the controlled release of the compounds into the matrix of the coating, thereby prolonging the effectiveness of the coating and reducing the amount of compounds necessary to produce the antifouling effect. Encapsulation into such slow release materials also may protect spinosyns from the harsh chemical milieu of the coating and would reduce their degradation while trapped in the resin, if susceptible to degradation. Other traditional methods for encapsulation can be used. For example, the antifouling agent particles can be microcoated, e.g., where the particles are coated with specially designed polymers in a fluidized bed reactor. The thickness of the coating material can be monitored and controlled by the dynamic operating conditions such as air flow, feed flow, temperature, nozzle size, substrate and the like. Another possible method is molecular inclusion wherein a hydrophobic antifouling agent is encapsulated within the "hydrophobic structure" of a host molecule such as beta-cyclodextrin. Another method of encapsulation is spray drying and coacervation of antifouling agents; this method encapsulates the antifouling agent in a well-defined glassy matrix made of carbohydrates and polymers.

While not wishing to be bound to a specific theory regarding the mechanism of action, it is believed that spinosyns present in the antifouling composition of this invention, function by producing a hostile environment at the surface of a coated or impregnated substrate which repels or affects the biofouling organisms, thereby preventing their attachment and growth on the coated surface. The inhibitory effect on the microorganisms may, however, be produced by inhalation, respiration, digestion or imbibition of the active agent by the microorganisms.

Also within the scope of this invention is any article having incorporated or having a surface coated, with a composition containing at least one spinosyn or derivative or salt or a combination thereof. The impregnated and/or coated articles of the invention can comprise any material that is in contact with fresh, salt, estuarine, brackish, sea or other bodies of water to which biofouling organisms are prone to attach, such as metal, wood, concrete, plastic, composite, and stone. Representative examples of articles which may benefit from a coating which inhibits attachment and growth of such organisms include boats and ships, for example their hulls, propellers, rudders, keels, centerboards, fins, hydrofoils, berthing facilities, such as piers and pilings, deck surfaces, buoys, wharves, jetties, fishing nets, industrial cooling system surfaces, cooling water intake, or discharge pipes, disalinization facilities, nautical beacons, floating beacons, floating breakwaters, docks, pipes, pipelines, tanks, water pipes in power stations, seaside industrial plants, fish preserving structures, aquatic constructions, port facilities, bridges, bells, plumbs, wheels, cranes, dredges, pumps, valves, wires, cables, ropes, ladders, pontoons, transponders, antennae, barges, periscopes, snorkels, gun mounts, gun barrels, launch tubes, mines, offshore rigging equipment, intake screens for water distribution systems and decorative or functional cement or stone formations.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements.

The following examples are provided to describe the invention in further detail. These examples are intended merely to illustrate specific embodiments of the compositions, methods and articles of the invention, and should in no way be construed as limiting the invention. These examples provide the results of tests conducted to determine the efficacy of certain spinosyns in inhibiting settlement of biofouling organisms. It will be apparent to those skilled in the art that embodiments described herein may be modified or revised in various ways without departing from the spirit and scope of the invention.

EXAMPLES

Example 1

Antimicrobial Assay Against Marine Bacteria Associated with *Balanus amphitrite*

The effect of spinosad as a bacteriostatic compound was tested against four bacterial species using standard agar diffusion techniques, as described by Avelin et al., J. Chem. Ecol., 19(10), 2155-67 (1993). The bacteria used in the test were as follows: *Aeromonas* sp (Ae); *Alcaligenes* sp (Al); *Flavobacterium* sp (F); and *Vibrio* sp (V);

The agar diffusion technique follows the original method by Acar (1980). In a sterilized petri dish 1 ml of 12 hour old nutrient broth culture, comprising of 3.7% of marine broth in distilled water, of each marine bacterial species was transferred along with 20 ml of antibiotic agar medium.

Sterilized Whatman No. 1 paper discs (6.25 mm diameter) were loaded with the test solution (2.4% w/w Tracer in distilled water) at concentrations calculated in pure spinosad ranging from $10^{-1}$ mg/10 µl to $10^{-4}$ mg/10 µl. Control discs were loaded with only the vehicle. After 24 hours of exposure to the test solution, the zone of inhibition, i.e. the area around the disc devoid of marine bacterial growth was measured by determining the distance from the edge of the disc to the edge of the area showing no bacterial growth (mm). The data showed in the Table 1 below demonstrate that spinosad solution has an inhibitory effect against these marine bacteria, even at several fold dilution:

TABLE 1

| | | Concentration | | | |
|---|---|---|---|---|---|
| Bacteria | Control | $10^{-1}$ mg/ 10 µl (10000 ppm spinosad) | $10^{-2}$ mg/ 10 µl (1000 ppm spinosad) | $10^{-3}$ mg/ 10 µl (100 ppm spinosad) | $10^{-4}$ mg/ 10 µl (10 ppm spinosad) |
| $Ae_1$ | — | 7.5 | 7 | 7 | 5.5 |
| $Ae_2$ | — | — | — | — | — |
| $Al_1$ | — | 8 | 6 | 6 | 6 |

TABLE 1-continued

| | | Concentration | | | |
|---|---|---|---|---|---|
| Bacteria | Control | $10^{-1}$ mg/ 10 µl (10000 ppm spinosad) | $10^{-2}$ mg/ 10 µl (1000 ppm spinosad) | $10^{-3}$ mg/ 10 µl (100 ppm spinosad) | $10^{-4}$ mg/ 10 µl (10 ppm spinosad) |
| $Al_2$ | — | 7 | 6.5 | 5.5 | 5.5 |
| $F_1$ | — | 7.5 | 6 | 6 | 6 |
| $F_2$ | — | 7.5 | 6 | 6 | 6 |
| $V_1$ | — | 8 | 5.5 | 5.5 | 5.5 |
| $V_2$ | — | 8 | 7 | 6 | 6 |

Example 2

Barnacle Cyprid Settlement Assay and $EC_{50}$ Determination

The barnacle, *Balanus amphitrite* Darwin, is the most ubiquitous hard fouling organism found in all marine ecosystems, particularly in ports visited by commercial shipping. The methods used in this evaluation have been described in detail in a number of publications (Rittschof D, Clare A S, Gerhart D J, Avelin Mary, Bonavetura J (1991) Barnacle in vitro assays for biologically active substances: toxicity and settlement assays using mass cultured *Balanus amphitrite* amphitrite Darwin. *Biofouling* 6:115-122.

The barnacle adults are cultured in the laboratory and allowed to spawn naturally. The larvae are harvested and grown in artificial culture systems until they reach the cyprid stage at which time the larvae become competent to attach to surfaces. Once attached, the cyprids transform into a pinhead barnacle, thus becoming permanently attached to the surface.

The sample solution tested was a 23.2% w/w solution of Tracer in distilled water (equivalent to 10% w/w in pure spinosad or 100 mg spinosad/ml). The sample was stirred prior to making serial dilutions.

The data are summarized in the Tables 2 and 3 below along with the calculations for the $EC_{50}$. At the highest concentration used (0.1 mg spinosad/ml), the cyprids were lethargic for a few hours after exposure to the test solution. However, the cyprids quickly recover and no mortality was observed at this dose. In fact, there was no mortality seen at all concentrations tested. There was no cyprid settlement from $10^{-1}$ to $10^{-4}$ mg/ml. Thereafter, there was dose dependent attachment from $10^{-5}$ and at lower concentrations, only reaching control values at $10^{-5}$ mg/ml. The $EC_{50}$ calculation via probit analysis show an $EC_{50}$ of $7 \times 10^{-8}$ mg/ml. The results show that spinosad is an effective, nontoxic inhibitor of the settlement of barnacle cyprids.

Additional notes to the data below: 1. Set means the total number of cyprid larvae that have settled and attached on the surface of the petri dish. 2. Non-Set means the total number of cyprids that remain swimming in the seawater and not settled on the surface. 3. Data are expressed as the percentage of cyprids that settled on the surface. 4. Data are summarized and the mean, standard deviation (SD) and the standard error of the mean (SE) are calculated for samples. 5. Tests were conducted in replicates of three dishes per study group; each dish containing anywhere from 75 to 100 cyprids.

Barnacle Settlement:

TABLE 2

| Concentration | Set | Non set | Metamorphosed but not set | Total | % of set |
|---|---|---|---|---|---|
| 1 | | | Control | | |
| a | 71 | 22 | 0 | 93 | 76 |
| b | 68 | 25 | 0 | 93 | 73 |
| c | 65 | 12 | 0 | 77 | 84 |
| Total | 204 | 59 | 0 | 263 | mean 78 |
| | | | | SD | 5.82 |
| | | | | SE | 2.60 |
| 2 | | | 0.1 mg spinosad/ml | | |
| a | 0 | 89 | 0 | 89 | 0 |
| b | 0 | 87 | 0 | 87 | 0 |
| c | 0 | 90 | 0 | 90 | 0 |
| Total | 0 | 275 | 0 | 266 | 0 |
| | | | | SD | 0.00 |
| | | | | SE | 0.00 |
| 3 | | | $10^{-2}$ mg spinosad/ml | | |
| a | 0 | 86 | 0 | 86 | 0 |
| b | 0 | 77 | 0 | 77 | 0 |
| c | 0 | 94 | 0 | 94 | 0 |
| Total | 0 | 257 | 0 | 257 | 0 |
| | | | | SD | 0.00 |
| | | | | SE | 0.00 |
| 4 | | | $10^{-3}$ mg spinosad/ml | | |
| a | 0 | 92 | 0 | 92 | 0 |
| b | 0 | 87 | 0 | 87 | 0 |
| c | 0 | 81 | 0 | 81 | 0 |
| Total | 0 | 260 | 0 | 260 | 0 |
| | | | | SD | 0.00 |
| | | | | SE | 0.00 |
| 5 | | | $10^{-4}$ mg spinosad/ml | | |
| a | 0 | 90 | 0 | 90 | 0 |
| b | 0 | 72 | 0 | 72 | 0 |
| c | 0 | 89 | 0 | 89 | 0 |
| Total | 0 | 251 | 0 | 251 | 0 |
| | | | | SD | 0.00 |
| | | | | SE | 0.00 |
| 6 | | | $10^{-5}$ mg spinosad/ml | | |
| a | 7 | 90 | 1 | 98 | 7 |
| b | 7 | 69 | 3 | 79 | 9 |
| c | 10 | 71 | 2 | 83 | 12 |
| Total | 24 | 230 | 6 | 260 | 9 |
| | | | | SD | 2.49 |
| | | | | SE | 1.11 |
| 7 | | | $10^{-6}$ mg spinosad/ml | | |
| a | 9 | 90 | 2 | 101 | 9 |
| b | 20 | 69 | 1 | 90 | 22 |
| c | 27 | 63 | 6 | 96 | 28 |
| Total | 56 | 222 | 9 | 287 | 20 |
| | | | | SD | 9.84 |
| | | | | SE | 4.40 |
| 8 | | | $10^{-7}$ mg spinosad/ml | | |
| a | 28 | 57 | 4 | 89 | 31 |
| b | 29 | 53 | 4 | 86 | 34 |
| c | 32 | 41 | 3 | 76 | 42 |
| Total | 89 | 151 | 11 | 251 | 35 |
| | | | | SD | 5.61 |
| | | | | SE | 2.51 |
| 9 | | | $10^{-8}$ mg spinosad/ml | | |
| a | 41 | 31 | 7 | 79 | 52 |
| b | 56 | 37 | 6 | 99 | 57 |
| c | 40 | 33 | 7 | 80 | 50 |
| Total | 137 | 101 | 20 | 258 | 53 |
| | | | | SD | 3.38 |
| | | | | SE | 1.51 |
| 10 | | | $10^{-9}$ mg spinosad/ml | | |
| a | 61 | 33 | 3 | 97 | 63 |
| b | 60 | 37 | 1 | 98 | 61 |
| c | 72 | 30 | 1 | 103 | 70 |
| Total | 193 | 100 | 5 | 298 | 65 |
| | | | | SD | 4.61 |
| | | | | SE | 2.06 |
| 11 | | | $10^{-10}$ mg spinosad/ml | | |
| a | 75 | 22 | 0 | 97 | 77 |
| b | 73 | 20 | 1 | 94 | 78 |
| c | 66 | 26 | 1 | 93 | 71 |
| Total | 214 | 68 | 2 | 284 | 75 |
| | | | | SD | 3.77 |
| | | | | SE | 1.69 |
| 12 | | | $10^{-11}$ mg spinosad/ml | | |
| a | 76 | 22 | 1 | 99 | 77 |
| b | 77 | 18 | 3 | 98 | 79 |
| c | 71 | 23 | 4 | 98 | 72 |
| Total | 224 | 63 | 8 | 295 | 76 |
| | | | | SD | 3.15 |
| | | | | SE | 1.41 |

$EC_{50}$ Calculations

TABLE 3

PROBIT ANALYSIS:
Barnacle Settlement

DATA AS INPUT

| DOSE | NO. TESTED | NO. RESPONDING |
|---|---|---|
| 0.000001 | 287 | 231 |
| 0.0000001 | 251 | 162 |
| 1E−08 | 258 | 111 |
| 1E−09 | 298 | 105 |
| 1E−10 | 284 | 70 |
| 1E−11 | 295 | 71 |

| | |
|---|---|
| PROPORTION OF CONTROLS RESPONDING = | .22 |
| SLOPE = | .5839765 |
| INTERCEPT = | 9.172569 |
| VARIANCE SOLPE = | 2.301465E−03 |
| LOG. ED50 = | −7.145098 |
| 95% CONFIDENCE INTERVAL = | −6.95896−−7.326811 |
| VARIANCE LOG. ED50 = | 8.517865E−03 |
| CHI 2 = 2.198044 | DF = 4 |

95% CONFIDENCE INTERVAL = 1.099107E−07−4.711828E−08
$ED_{50}$ = 7.159825E−08
$ED_{50}$ = 0.00000007 mg/ml ($7 \times 10^{-8}$ mg/ml)

Example 3

Inhibition of Fouling Organisms Using a Paint Composition Containing Spinosad

Two PVC square panels 15×15 cm were painted as follows: one side with a composition containing 11.43% w/w Tracer (5% pure spinosad) and 88.57% w/w white conventional acrylic paint (free of any preservative or other antifouling agent) and the other side with the paint only (control paint). The coated panels were submerged in a fouled marine environment, in Olympic marine in Sounion, Greece, at a distance of approximately 60 cm from the water surface to determine the degree of resistance provided by the test coatings against fouling. The panels were exposed to seawater for 10 weeks. At the end of the exposure period, the panels were inspected for fouling.

Control Paint Side Had Appreciable Fouling

Side treated with composition with 5% spinosad, no appreciable fouling attachments Example 4

Inhibition of the Growth of the Fouling Microalgae, *Dunaliella tertiolecta*, by Spinosad Emulsion A water emulsion containing 23.2% w/w Tracer®=10% spinosad was used at the start of this assay. *Dunaliella tertiolecta* was maintained in stock cultures in 20 ml test tubes as seed cultures and maintained on seven day transfer cycle. The marine micro-algae were inoculated into 250 ml conical flasks containing 100 ml of filtered, sterilized seawater in F/2-Guillard-1975 growth medium. The initial 10% spinosad emulsion (coded Entarco 8205 10%), was further dissolved in distilled water and added at various concentrations to each algal culture for final concentrations ranging from $10^{-2}$ mg spinosad/ml to $10^{-9}$ mg spinosad/ml. Controls consisted of algal culture without the test solution. Each test group was comprised of 3 flasks.

The typical culture goes through four phases. Lag phase is characterized by little or no multiplication of the cells. Log phase or exponential phase is when there is a rapid increase in the rate of cell division. During the next phase, called stationary phase, the number of living cells remain constant and there is no further growth. In the decline phase, the cells begin the process of death or senescence. The growth of the algal cells in each flask was counted each day by haemocytometer. The entire growth and decline of the culture in the presence or absence of spinosad was determined (Targett, 1988 Allelochemistry in marine organisms: Chemical fouling and antifouling strategies).

Flask culture environmental conditions:

| Lighting |
| --- |
| Cycle : 12 hours light/12 hours dark |
| Type: fluorescent bank: 2-F20T12 Westinghouse cool white |
| Intensity: 133-299 uEin/sec/cm$^2$ |
| Temperature: 20° C. |
| Water |

| |
| --- |
| Type: Aged, sterilized |
| Salinity: 30 ppt |
| Total volume: 250 ml |
| Flask size: 1 L Pyrex glass Erlenmeyer flask |
| Concentration |

| |
| --- |
| Seeding density: 2.5-5.0 × 10$^4$ cells per ml |
| Nutrients: 1 ml stock nutrients per liter of seawater |
| Time to bloom: 6-7 days |
| Bloom density: 1-3 × 10$^6$ cells per mal |

Figure 1:
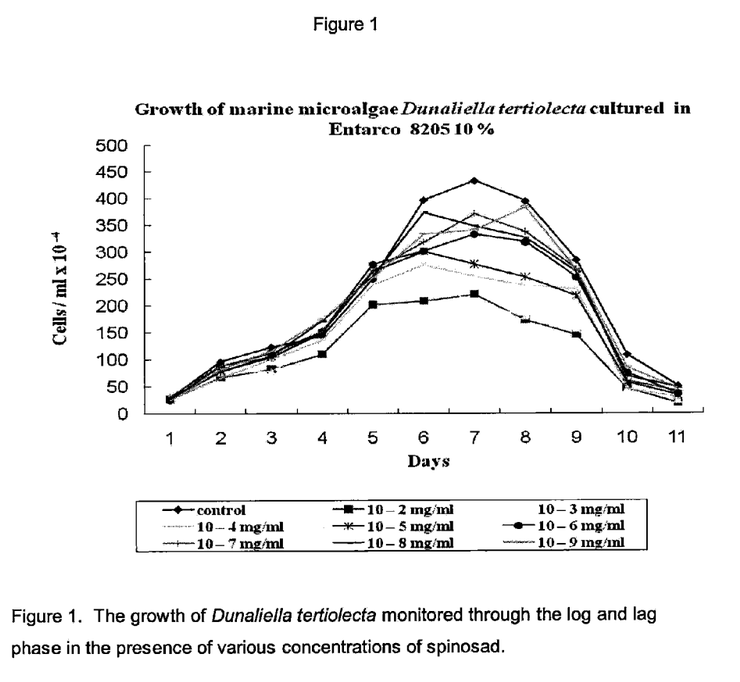
FIG. 1 shows a graphical representation of the growth of *Dunaliella tertiolecta* monitored through the log and lag phase in the presence of various concentrations of spinosad.

The data set forth in FIG. 1 show that spinosad has significant microalgae inhibitory properties which are dose dependent.

Example 5

40 Weeks Static Immersion Test

Figure 2:
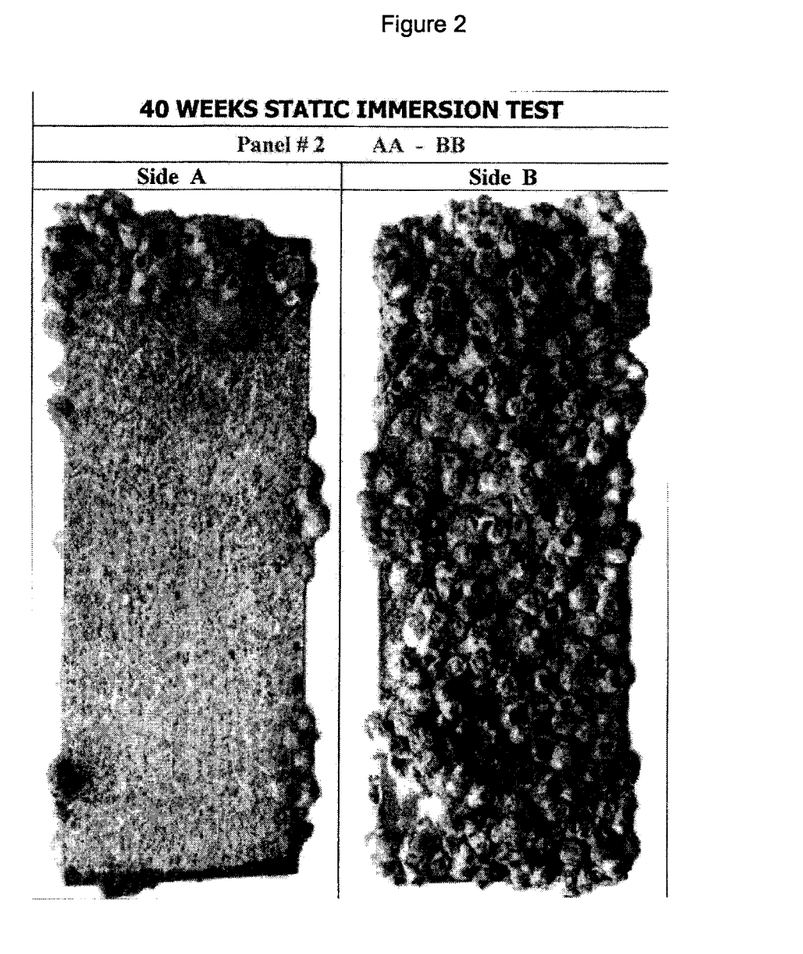
FIG. 2 shows a photograph of a 40 weeks static immersion test for Panel #2 comparing Panel ID AA and BB from Table 4 (side A=AA, side B=BB).
Figure 3:
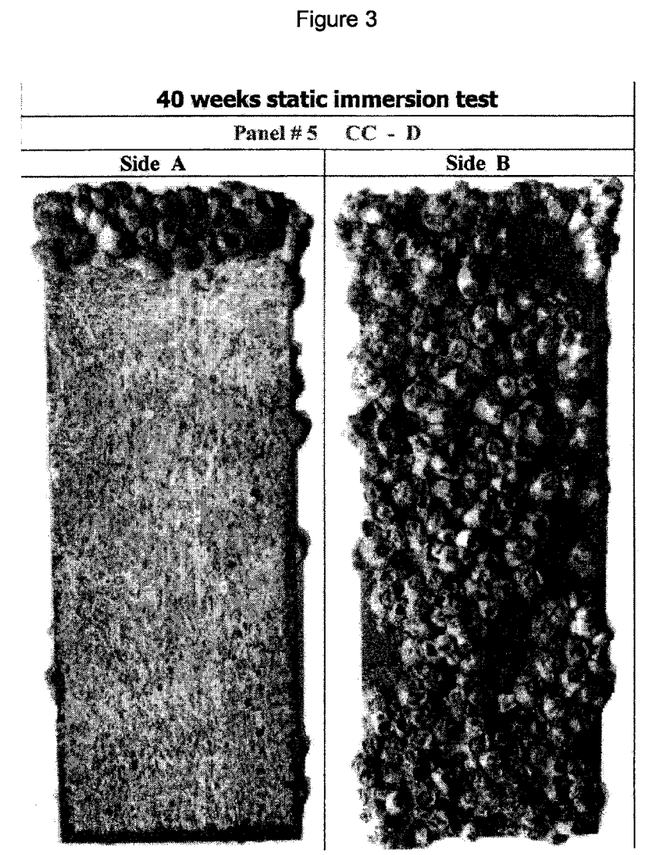
FIG. 3 shows a photograph of a 40 weeks static immersion test for Panel #5 comparing Panel ID CC and DD from Table 4 (side A=CC, side B=DD).

Test panels of approximate dimensions 7.6×20.4 cm were coated and labeled as follows: Side AA was coated with a paint formulation consisting of 77.3% w/w white conventional acrylic paint (free of any preservative or other antifouling agent) and 22.7% w/w Tracer® product, (formulation content in spinosad 10%). Side BB was coated with the carrier only (the paint without spinosad) as a control panel. Side CC was coated with a paint formulation consisting of 88.6% w/w white conventional acrylic paint (free of any preservative or other antifouling agent) and 11.4% w/w Tracer® product, (formulation content in spinosad 5%). Side DD was not coated with any material. On the labeled surface of all panels there was no coating. The panels were placed in the holders of a floating platform and remained continuously submerged in Tuticorin Bay, India, for a period of 40 weeks. The panels were examined for a few minutes every month and immediately re-immersed after photography. The data obtained are set for in the table 4 below and represented by FIGS. 2 and 3. These data clearly demonstrate that coating compositions containing spinosyns and spinosad in particular, are for a long time very effective in preventing the attachment of fouling organisms, especially hard fouling like barnacles, on the surfaces of underwater structures to which the composition is applied. Photos of some panels at the end of this test are also attached hereto.

TABLE 4

Static 40 weeks immersion test:

| PANEL NO | PANEL ID | SIDE | NUMBER OF SINGLE BARNACLES | % OF SURFACE COVERED BY BARNACLES | NUMBER OF BARNACLES ON THE LABELED SURFACE | MAXIMUM DIAMETER IN MM | NO OF OYSTERS | TUBE WORMS |
| --- | --- | --- | --- | --- | --- | --- | --- | --- |
| 1 | AA | a | 13 | — | 40 | 10 | — | — |
|   | BB | b | ++++ | 80 | 21 | 18 | 5 | 5 |
| 2 | AA | a | 16 | — | 33 | 8 | 1 | — |
|   | BB | b | ++++ | 85 | 30 | 18 | 2 | 6 |
| 3 | AA | a | 6 | — | 40 | 18 | — | — |
|   | BB | b | ++++ | 70 | 32 | 18 | 1 | 6 |
| 4 | CC | a | — | — | 27 | 9 | — | 3 |
|   | DD | b | ++++ | 60 | 20 | 18 | — | 1 |

TABLE 4-continued

Static 40 weeks immersion test:

| PANEL NO | PANEL ID | SIDE | NUMBER OF SINGLE BARNACLES | % OF SURFACE COVERED BY BARNACLES | NUMBER OF BARNACLES ON THE LABELED SURFACE | MAXIMUM DIAMETER IN MM | NO OF OYSTERS | TUBE WORMS |
|---|---|---|---|---|---|---|---|---|
| 5 | CC | a | 4 | — | 30 | 10 | — | — |
|   | DD | b | ++++ | 60 | 23 | 18 | 1 | 2 |
| 6 | CC | a | — | — | 24 | 6 | — | — |
|   | DD | b | ++++ | 60 | 33 | 18 | — | — |

Note 1:
when barnacles are too many to count (symbol: ++++), we refer to the % of panel surface covered by them, at next column.
Note 2:
the labelled area has no coating, therefore barnacles can adhere to this area.

I claim:

1. A method of protecting a marine or freshwater submerged article from adhesion by fouling organisms chosen from organisms belonging to the family Balanidae; bacteria belonging to the species *Vibrio* sp., *Flavobacterium* sp., *Alcaligenes* sp, and *Aeromonas* sp.; and diatoms, the method comprising:
applying to said article a marine or freshwater antifouling coating composition comprising an effective amount of at least one spinosyn or salt thereof and a carrier, wherein said composition is effective to inhibit adhesion of said fouling organisms to said article.

2. The method of claim 1, wherein the at least one spinosyn is chosen from spinosad, spinetoram, and butenyl spinosyn.

3. The method of claim 1, wherein said marine or freshwater fouling organisms are chosen from barnacles belonging to the genus *Balanus*.

4. The method of claim 1, wherein the composition comprising at least one spinosyn further comprises an additional antifouling active ingredient chosen from antifouling biocides, microbicides, natural origin antifoulants, antifouling metal salts, bactericides, fungicides, algaecides, insecticides and antibiotics, including free or encapsulated forms of the above or mixtures thereof.

5. The method of claim 1, wherein the coating composition comprises a film-forming polymer binder.

6. The method of claim 5, wherein said coating composition is a paint, varnish, primer, or sealant.

* * * * *